US008005700B2

(12) United States Patent (10) Patent No.: US 8,005,700 B2
Amitabh et al. (45) Date of Patent: Aug. 23, 2011

(54) CUSTOMER RELATIONSHIP MANAGEMENT SYSTEM WITH COMPLIANCE TRACKING CAPABILITIES

(75) Inventors: Prasanna Amitabh, Fairfax, VA (US); Jeffrey D. Carpenter, Alexandria, VA (US); Francis J. Cotter, Arlington, VA (US); Cynthia N. Gee, Arlington, VA (US)

(73) Assignee: International Business Machines Corporation, Armonk, NY (US)

( * ) Notice: Subject to any disclaimer, the term of this patent is extended or adjusted under 35 U.S.C. 154(b) by 1019 days.

(21) Appl. No.: 10/630,392

(22) Filed: Jul. 30, 2003

(65) Prior Publication Data

US 2005/0027575 A1 Feb. 3, 2005

(51) Int. Cl.
*G06Q 99/00* (2006.01)
(52) U.S. Cl. ............... 705/7.11; 705/2; 705/3; 705/4
(58) Field of Classification Search .............. 705/7.11, 705/2, 3, 4
See application file for complete search history.

(56) References Cited

U.S. PATENT DOCUMENTS

| | | | |
|---|---|---|---|
| 5,537,141 A | 7/1996 | Harper et al. | |
| 5,823,788 A | 10/1998 | Lemelson et al. | |
| 6,074,216 A | 6/2000 | Cueto | |
| 6,105,055 A | 8/2000 | Pizano et al. | |
| 6,301,462 B1 | 10/2001 | Freeman et al. | |
| 6,310,941 B1 | 10/2001 | Crutcher et al. | |
| 6,470,170 B1 | 10/2002 | Chen et al. | |
| 6,507,865 B1 | 1/2003 | Hanson et al. | |
| 6,700,575 B1* | 3/2004 | Bovarnick et al. ............ 345/440 |
| 6,704,015 B1* | 3/2004 | Bovarnick et al. ......... 345/440.2 |
| 7,130,807 B1* | 10/2006 | Mikurak ........................... 705/7 |
| 7,340,433 B1* | 3/2008 | Kay et al. ........................ 705/38 |
| 2002/0042751 A1* | 4/2002 | Sarno ............................... 705/26 |
| 2002/0133392 A1* | 9/2002 | Angel et al. .................... 705/10 |
| 2003/0055684 A1* | 3/2003 | Jaskolski et al. ................. 705/3 |
| 2003/0055737 A1* | 3/2003 | Pope et al. ..................... 705/26 |
| 2003/0229525 A1* | 12/2003 | Callahan et al. .................. 705/7 |
| 2004/0098285 A1* | 5/2004 | Breslin et al. .................... 705/1 |
| 2004/0215468 A1* | 10/2004 | Doeberl et al. ................... 705/1 |
| 2006/0293942 A1* | 12/2006 | Chaddha et al. ................. 705/8 |
| 2007/0283171 A1* | 12/2007 | Breslin et al. ................. 713/193 |
| 2009/0063246 A1* | 3/2009 | Lurie ............................... 705/9 |
| 2009/0089125 A1* | 4/2009 | Sultan .............................. 705/7 |

FOREIGN PATENT DOCUMENTS

WO WO 2004107094 * 12/2004

OTHER PUBLICATIONS

Shen, K.H.W. et al, WAP mail service and short message service for mobile CRM [customer relationship management], Dec. 11, 2000-Dec. 13, 2000, Multimedia Software Engineering, 2000. Proceedings. International Symposium on Digital Object Identifier: 10.1109/MMSE.2000.897212, Publication Year: 2000 , pp. 201-207.*

* cited by examiner

*Primary Examiner* — Akiba K Robinson Boyce
(74) *Attorney, Agent, or Firm* — Douglas Lashmit; Hoffman Warnick LLC

(57) ABSTRACT

A customer relationship management (CRM) system and method accessible via a network. The system comprises: a user interface that provides distributed access for customers and support providers to case information within the CRM system; a case management system for managing customer cases, wherein the case management system includes a system for assigning cases to different tiers within a support provider hierarchy; and a compliance tracking system that determines customer compliance and provides a compliance indicator on customer case management pages.

26 Claims, 5 Drawing Sheets

|       |       |       |       |       |
|-------|-------|-------|-------|-------|
| HOME  | PROGRAMS | RESOURCES | ABOUT AUAO | |

NEW CASE #   [ 007 ]                                                  25

1
- FIRST NAME [POPULATED FROM t_users TABLE]   MIDDLE NAME [POPULATED FROM t_users TABLE]
- LAST NAME [POPULATED FROM t_users TABLE]    SOCIAL SECURITY NUMBER [POPULATED FROM t_users TABLE]

26

2
- CAMPUS (COURSE IS BEING TAKEN) [USER ENTERS DATA]
- COURSE DESCRIPTION [USER ENTERS DATA]   [USER ENTERS DATA]
  SUBJECT: (E.G. ENG, MTH, REL, ETC)   COURSE #: (E.G. 1301, 101, 4521)
- COURSE START DATE [USER ENTERS DATA]   COURSE END DATE [USER ENTERS DATA]
- INSTRUCTOR [USER ENTERS DATA]

3
- RISK LEVEL [USER SELECTS DATA FROM DROP DOWN MENU ▽]
- CASE CATEGORY [USER SELECTS DATA FROM DROP DOWN MENU ▽]

28

CASE DETAILS
[USER ENTERS DATA]

ACTIONS TAKEN
[USER ENTERS DATA]

29

4
RECOMMENDATIONS
[USER ENTERS DATA]

[SUBMIT]  [CANCEL]

*FIG. 3*

CRM SEARCH RESULTS

RESOURCES
ACES LINKS
TUTORIALS
TRAINING
ELIGIBILITY
CHECKLIST
ACES INFORMATION
ASSET MANAGEMENT
IMPORTANT FORMS
FAQS
RELS DESK
CAREER OPTIONS

SEARCH RESULTS FOR ARRON EVERETT SMITH:

| | |
|---|---|
| CUSTOMER TYPE: | STUDENT |
| CUSTOMER NAME | AARON EVERETT SMITH |
| SOCIAL SECURITY NUMBER | 445021430 |
| EMAIL | aaron.smith017@earmyu.com |
| MAILING ADDRESS | 1967-C XYZ CIRCLE |
| CITY | WAHLAWA |
| STATE | HAWAII |
| ZIP | 96780 |
| COUNTRY | USA |
| PHONE | 8086240699 |
| INSTALLATION | SCHOFIELD BARRACKS |
| INSTALLATION MAJOR SUB UNIT | |
| SERVICE BRANCH | ARMY ENLISTED |
| CURRENT INSTALLATION | SCHOFIELD BARRACKS |
| BASD | 3/19/96 |
| PERD | 1/8/92 |
| EXPECTED SEPARATION DATE | 2/16/04 |

— 32

STUDENT STATUS — PROSPECTIVE STUDENT - NOT ENROLLED IN AUAO
ACTIVE? — TRUE

ALTERNATE PHONE 1: 888-645-0877   ALTERNATE PHONE 2: 888-645-0872

PROSPECTIVE STUDENT - NO STUDENT AGREEMENT

NO STUDENT AGREEMENT UPLOADED

— 34

RIGHT TRACK DISPLAY

12 SEMESTER HOURS PROGRESS: 2
AT RISK IN CURRENT COURSE(S): 3

→ 40   — 36

HELP DESK CASE SUMMARY

CURRENT CASE(S) OPEN:
    CASE CATEGORY:    CASE NUMBER:    DATE OPENED:    LAST UPDATED:
CLOSED CASES:
    CASE CATEGORY:    CASE NUMBER:    DATE OPENED:    DATE CLOSED:

CASE SUMMARY — 42

DATE/TIME OPENED: 6/17/2002   OPENED BY: ED_Partner001

CASE CATEGORY: ABSENTEEISM

| CASE DETAILS: | ENTERED BY: | DATE |
|---|---|---|
| STUDENT MISSED FIRST WEEK OF CLASS. | ED_Partner001 | 6/17/2002 |
| STUDENT MISSED MID-TERM | ED_Partner001 | 7/1/2002 |

← 44

CASE DETAILS:

[ ENTER NEW CASE DETAILS HERE. ]

| ACTIONS TAKEN | ENTERED BY | DATE | |
|---|---|---|---|
| INSTRUCTOR ATTEMPTED TO CONTACT STUDENT VIA EMAIL | ED_Partner001 | 6/20/2002 | 2 |
| ESCALATED CASE TO LEVEL 3 RISK | ED_Partner001 | 7/1/2002 | |

← 46

ACTIONS TAKEN:

[ ENTER NEW ACTIONS TAKEN HERE. ]

RECOMMENDATIONS:  ← 48

[ ENTER NEW RECOMMENDATIONS HERE. ]

[SUBMIT] [CANCEL]  ← 50

*FIG. 5*

CUSTOMER RELATIONSHIP MANAGEMENT SYSTEM WITH COMPLIANCE TRACKING CAPABILITIES

BACKGROUND OF THE INVENTION

1. Technical Field

The present invention relates generally to customer relationship management (CRM) systems, and more specifically relates to a distributed CRM system having compliance tracking capabilities.

2. Related Art

Given the competitive nature of most industries, the ability to provide superior customer support services have become critical for success. However, as the products and services provided by many industries become more complex and distributed, the ability to effectively provide support services has become more and more challenging. For instance, there may exist numerous individuals in a given organization that have unique skill sets for handling different types of customer problems. However, such individuals may reside at different geographic locations, work different hours, and utilize different information technology (IT) systems. Moreover, customer service issues may be distributed across many different organizations or vendors, each having their own systems for handling customer problems.

In order to automate customer service problems, such as questions and problems related to purchased products and services, many organizations utilize some type of customer relationship management (CRM) tool. These tools allow the organization to enter customer information and related problems into a computer program or database so that the problems can be tracked and solved in an automated fashion. Using such tools, high volumes of issues can be centrally managed and addressed. However, as noted above, many providers of goods and services (i.e., products) have complex structures in which expertise about the products is distributed across different organizations and vendors. Unfortunately, current CRM tools are not equipped to provide distributed functionality.

Closely tied to almost all customer support services is the notion of compliance. For instance, has the customer completed any required maintenance, made the necessary upgrades, and/or fulfilled their obligations with respect to the purchased products? Moreover, is the customer under warranty or have they even paid for support services? Knowing these key pieces of information not only allows for better support, but such knowledge also allows the organization to generate additional revenue from the sale of new products to the customer. Unfortunately, current CRM tools lack any significant compliance tracking features.

Accordingly, a need exist for a CRM tool that can provide distributed functionality across different organizations and also provide compliance tracking for each customer.

SUMMARY OF THE INVENTION

The present invention addresses the above-mentioned problems, as well as others, by providing a distributed customer relationship management (CRM) tool that includes compliance tracking. In a first aspect, the invention provide a customer relationship management (CRM) system that is accessible via a network, comprising: a user interface that provides distributed access for customers and support providers to case information within the CRM system; a case management system for managing customer cases, wherein the case management system includes a system for assigning cases to different tiers within a support provider hierarchy; and a compliance tracking system that determines customer compliance and provides a compliance indicator on customer case management pages.

In a second aspect, the invention provides a method for providing customer relationship management (CRM) via a computer network, comprising the steps of: providing a network node that allows distributed access for customers and support providers to a CRM system; opening a new case within the CRM system when a customer issue occurs; adding the new case to a customer case management page; displaying a compliance indicator when the customer case management page is viewed; assigning the new case to a first tier support provider; determining if the first tier support provider can handle the new case; and escalating the new case to a second tier support provider if the first tier support provider cannot handle the case.

In a third aspect, the invention provides a program product stored on a recordable medium that provides a customer relationship management (CRM) tool via the web, comprising: a portal page for providing distributed access on the web for customers and support providers to case information within the CRM tool; a customer management module for managing customer cases and for assigning cases to different tiers within a support provider hierarchy; and a customer compliance module that tracks customer compliance and displays a compliance indicator on customer case management pages.

BRIEF DESCRIPTION OF THE DRAWINGS

These and other features of this invention will be more readily understood from the following detailed description of the various aspects of the invention taken in conjunction with the accompanying drawings in which:

FIG. 3 depicts a screenshot of a new case page in accordance with the present invention.

FIG. 4 depicts a screenshot of a case management page in accordance with the present invention.

FIG. 5 depicts a screenshot of a case details page in accordance with the present invention.

DETAILED DESCRIPTION OF THE INVENTION

Figure 1:
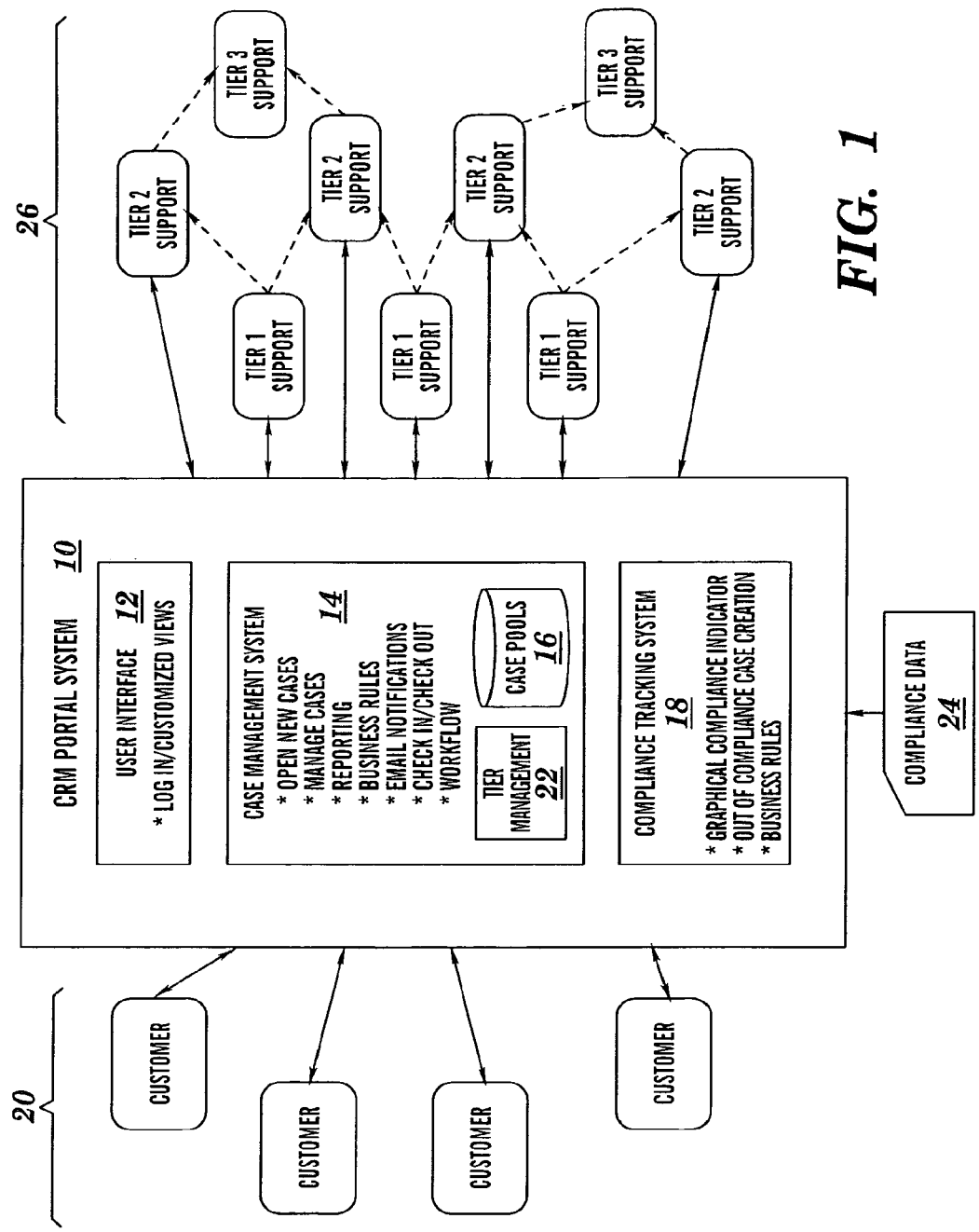
FIG. 1 depicts a CRM portal system in accordance with the present invention.

Referring now to the drawings, FIG. 1 depicts a customer relationship management (CRM) portal system 10 for managing customer issues over a computer network. The CRM portal system 10, could be used in any industry, e.g., retail/wholesale sales, academia, medical services, manufacturing, government, etc., where customers of goods and services may require ongoing support. CRM portal system 10 may be implemented on a computer network, such as the Internet or an intranet, to allow both customers 20 and support providers 26 accessibility anywhere in the world. In an exemplary embodiment, CRM portal system may be implemented as a web page portal on the World Wide Web (web). By providing a centralized network node or web portal, support providers 26 can be distributed in any manner and are not therefore subject to previous limitations, e.g., they may reside at different physical locations, utilize different IT technologies, belong to different organizations, work for different divisions, etc.

CRM portal system 10 includes a user interface 12 that allows a "network" of users, i.e., customers 20, support providers 26, administrators, etc., easy and user-friendly access to CRM information. As explained in further detail below, whenever a customer issue is raised, a new case is created. Users can then view and manage case information via the user interface 12. In a web embodiment, information may be downloaded and displayed to users as web pages in a web browser, thereby allowing access from virtually anywhere.

FIG. 3 depicts a screenshot of a new case page 25. New case page 25 includes: a customer details section 26 having fields for entering general customer details; drop down menus 28 for assigning an initial risk level and case category, and data fields 29 for entering case details, actions taken, and recommendations. Each case has a unique case page that may include a unique identifier, e.g., "007."

Within the interface 12, each customer has their own case management page, where details of any open or resolved cases may be listed. For instance, FIG. 4 depicts an exemplary case management page 30 for a customer (in this case a student). The case management page includes customer information 32, such as name, address, etc.; status information 34; compliance information 36; and a case summary 38. From the case management page 30, a user can select and display specific cases from the case summary 38, e.g., by clicking on the current or closed case links the user can navigate to specific case pages. In general, anytime a user needs case information about a customer, they will be brought to a case management page.

As shown in FIG. 5, a case summary page 42 is shown for a specific customer case. On this screen, the user, e.g. a service provider, can view case details 44, view previous actions taken 46, enter new actions to be taken 48, or enter recommendations to be taken 50. The service provider can submit new actions or recommendations by clicking a submit button, 50 on the page. From here, a service provider can escalate the case to a next tier level. When such an action is taken, the email notifications can be automatically generated. While a customer would have access to their own case detail pages, they generally would not have the ability to take actions or submit recommendations.

Thus, customers, support providers, and administrators may be granted different views and functions for displaying and managing CRM information. For instance, a customer may only be able to view their own cases, a support provider may be able to display and alter all cases that they currently "own," and an administrator may be able to view all cases in the system. The number and types of views available to different users may be dictated by a set of business rules and determined based on log in parameters. Moreover, the type and format of the case information presented via user interface 12 is not limited, and will generally depend on the specific CRM application being implemented.

Referring again to FIG. 1, cases are handled by case management system 14 within CRM portal system 10. Case management system 14 provides all of the features and tools for managing cases, including opening new cases, assigning and tracking cases, providing reports, generating email notifications, providing check-in/check-out capabilities, etc. In addition, case management system 14 includes a tier manager 22, which manages how cases are assigned to different tiers of support providers 26. In general, when a new case is first opened, it is placed into a case pool 16, where it can be viewed along with all other open cases. From the case pool 16, it is assigned to a "tier 1" support provider. Once assigned to a "tier 1" support provider, the case is then checked out and owned by that provider, and will appear within that provider's list of active cases. Accordingly, no other providers can work on the case. If the provider cannot resolve the case, e.g., because their shift ends, the case can be checked back into the case pool 16 for some other tier 1 service provider to work on. When a tier 1 service provider owns a case, he or she can submit an action on the status of the case, resolve the case, or escalate the case to a tier 2 support provider.

Tier manager 22 includes built in escalation procedures that allow cases to be categorized and escalated/de-escalated among a hierarchy of service providers. In the example shown in FIG. 1, three levels of services providers are depicted, tier 1, tier 2 and tier 3. In a typical CRM environment, the tier 1 support provider may have generalized knowledge of the goods and services being used by the customer, and can therefore resolve many basic issues. However, in the event that issue requires specialized knowledge beyond the capabilities of the tier 1 support provider, the case can be escalated to a tier 2 service provider. In the event that even more specialization is required, the case could be further escalated to a tier 3 service provider. As described below, cases can also be escalated/de-escalated automatically if the customer is not in compliance with some predefined set of requirements, e.g., they failed to perform some routine maintenance, fail an exam, etc.

Regardless of who owns a case, the customer and all users of the network may have the ability to view a customer's case management page to check the status of any open cases and to submit comments on that case. All comments submitted are stamped with a time, date, and author stamp within the case notes for the customer and others in the network to review as the case is being resolved.

The case owner can also return a case to a customer in the event that not enough information was provided by the customer to diagnose the issue and to resolve the case. The customer may be sent an automated email to notify them that a case has been returned for more information. The customer is able to view the case, read comments from the case owner about what additional information is required, and then submit answers to those questions via the CRM Portal System 10. Case owners, i.e., providers, are also able to view a customer's case management page 30 when working on a customer's case so that they can make sure a new case is not related to an existing case or a previously closed case.

Customized email receipts and reminders may be sent at any stage, e.g., when cases have been opened, closed, escalated or returned to a customer for more information. Each customer can access their case management page in their view of the portal to display all of their cases that are open or have been closed in the past. The customer can access this page at any time to view progress on open cases or case resolutions for closed cases. The customer can submit additional notes to their opened or closed cases at any time, which are published to the case with a date and time stamp.

CRM portal system 10 also includes a compliance tracking system 18 that tracks compliance parameters for each customer. The type of compliance parameters will depend on the applicable industry. For instance, in an academic environment, parameters may include whether a student is behind in a particular course, has failed an exam, has too many absences, etc. In a technical support environment, parameters may include whether the customer has paid for a service agreement, whether any routine maintenance has been performed, etc. In a medical environment, parameters may include whether the patience has filled necessary prescriptions, attended therapy sessions, etc. Obviously any parameters can be implemented without departing from the scope of the invention.

When a customer has a compliance issue, a compliance indicator is displayed on the customer management page 30. For instance, as shown in FIG. 4, one or more traffic lights 40 are displayed. The traffic light 40 will display a green light if no compliance issues exist, a yellow light if the customer is at risk of becoming out of compliance, and a red light if the customer is out of compliance. By clicking on the traffic light, the details of the compliance issue can be displayed. Accordingly, service providers 26, as well as customers, are always on notice when a compliance issue exists.

Compliance data 24 can originate from any source and be loaded to CRM portal system 10 in any manner. For instance, the data 24 may be uploaded via an FTP batch operation from any organization participating in the network. For instance, a university could upload student test information; a vendor could upload maintenance information for customers using the vendor's products; a physical therapist could upload progress data for a patient, etc. The compliance data for each customer can then be compared to some predetermined levels to determine whether a compliance issue exists. If an issue does exist, the compliance indicator 40 can be updated to reflect the appropriate risk level.

As noted above, compliance tracking system 18 can cause cases to be automatically created or escalated if a compliance issue exists. User defined business rules may be utilized to dictate what constitutes a situation when a new case should be opened, closed, escalated, or de-escalated.

Figure 2:
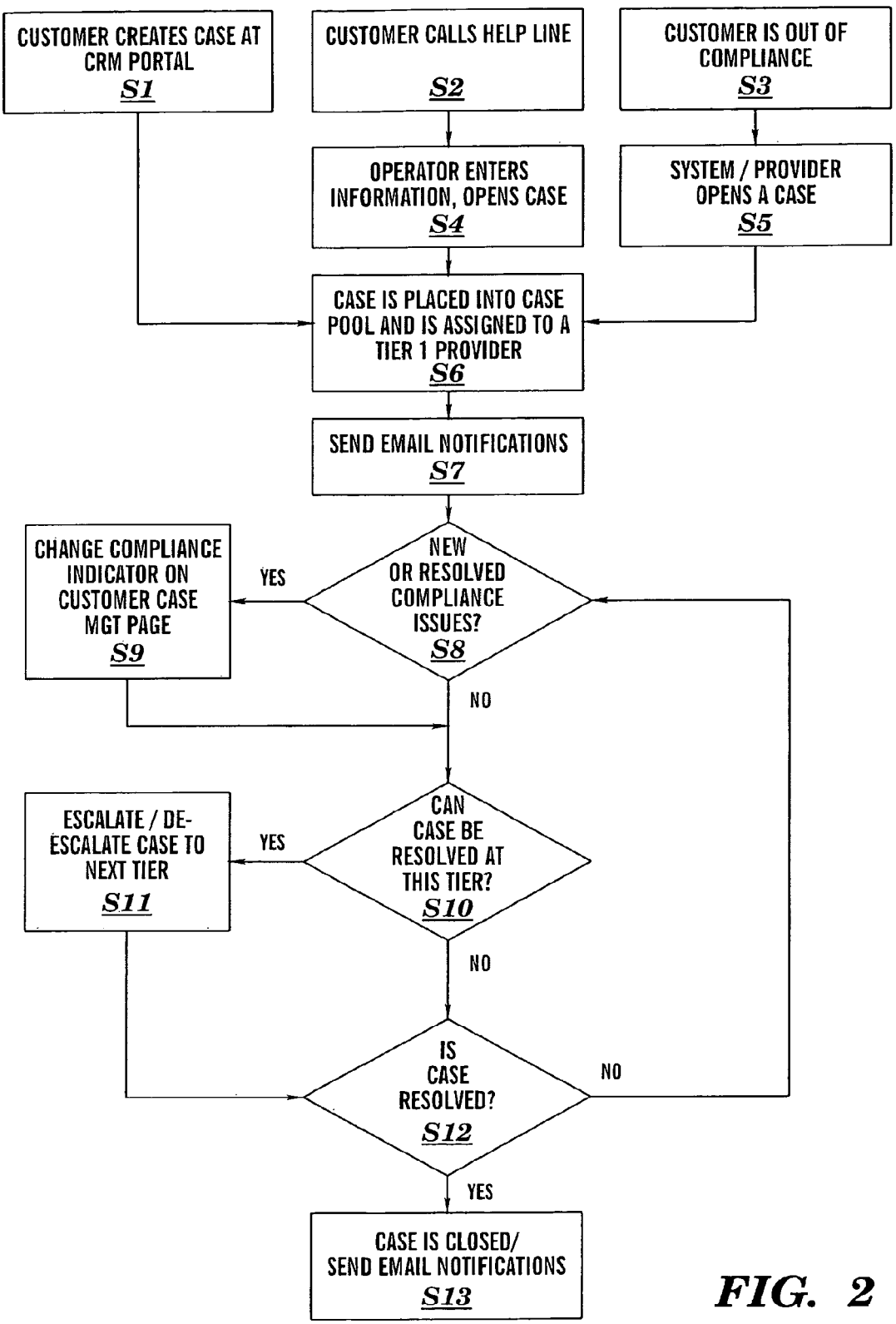
FIG. 2 depicts a flow diagram of a method of implementing a CRM system in accordance with the present invention.

Referring now to FIG. 2, a flow diagram of an exemplary method of implementing the present invention is shown. As noted above, there are several ways in which a new case can be opened. At step S1, the customer visits the CRM portal and creates a case; at step S2, a customer can call a help line, and then an operator can open a case at step S4; or if a customer is out of compliance (step S3), a case can get opened by the system or by a service provider at step S5. Once a case is opened, it is placed into a case pool, and the case is assigned to a tier 1 service provider at step S6. The service provider may "check out" the case so that no other service providers can enter data or work on the case. Checking out the case also allows the service provider to work off-line if desired. At this point, an email notification can be sent to the customer, letting the customer know that a case has been assigned to a service provider. Note that the timing, addressing and content of email notifications can be easily changed and configured to meet the particular needs of the particular CRM application.

Next, at step S8, a check can be made to see if the customer has any new compliance risks or issues. If so, then the compliance indicator on the customer management page can be updated at step S9 to reflect the appropriate risk level. Next, at step S10, a determination is made whether the current service provider can resolve the case—in this case, by a tier 1 service provider. If the current service provider cannot resolve the case, the case can be escalated (or de-escalated) at step S11 to a next tier, e.g., tier 2. Otherwise the case stays at the current tier. Next, at step S12 if the case is resolved by the current service provider, the case is closed and appropriate email notifications can be sent at step S13. If the case is not resolved, the logic can loop back to step S8, where the compliance and tier level can be repeatedly checked until the case is resolved. It should be understood that the order and general logic shown in FIG. 2 is for exemplary purposes only, and that various alterations and modifications could be implemented without departing from the scope of the invention.

In one exemplary embodiment, the CRM portal system 10 may be utilized in an academic setting, where various colleges and universities at various different locations may teach courses. When a customer, i.e., a student, has a problem, they can log onto the CRM portal system and open a new case. From there, the case is submitted to a pool for assignment to a tier 1 support provider. Depending on the nature of the problem, e.g., administrative versus academic, the case will be assigned to an appropriate service provider. Thus, in the case of an academic problem, the case may be assigned to a graduate student to help resolve the problem. If the tier 1 service provider could not resolve the problem, the case could be escalated to a tier 2 service provider, e.g., a professor.

In addition, compliance tracking system 18 may be implemented to determine whether the student is "behind pace," to meet preset goals. If the student were behind pace, the compliance indicator on the student's case management page would reflect the appropriate risk level. The compliance tracking system 18 may work by pulling data from sequel tables and using business logic to determine if the student is on pace to meet predefined objectives, e.g., 12 semester hours in two years. By clicking on the compliance indicator 40, information can be displayed to tell the student exactly how many courses have been completed and how many are in progress.

In this context, the compliance tracking system 18 works allows professors or administrators at participating universities to log into the CRM portal system 10, enter a student's ID into the case management system 14, and then create a special kind of case called a "behind pace in course" case for a student. The case management system 14 may use information in enrollment tables to only allow an instructor to create a case for a student who is enrolled at the university where the instructor is employed. The instructor can determine if the student is behind pace because of poor grades or absenteeism, and select a degree of risk for the student for failing his or her course. Upon submitting the case, the student receives an automated email notifying him or her that they are behind pace in a course, it also submits a report to a program mentor responsible for contacting the student, and it updates the compliance indicator on the student's case management page.

It is understood that the systems, functions, mechanisms, methods, and modules described herein can be implemented in hardware, software, or a-combination of hardware and software. They may be implemented by any type of computer system or other apparatus adapted for carrying out the methods described herein. A typical combination of hardware and software could be a general-purpose computer system with a computer program that, when loaded and executed, controls the computer system such that it carries out the methods described herein. Alternatively, a specific use computer, containing specialized hardware for carrying out one or more of the functional tasks of the invention could be utilized. The present invention can also be embedded in a computer program product, which comprises all the features enabling the implementation of the methods and functions described herein, and which—when loaded in a computer system—is able to carry out these methods and functions. Computer program, software program, program, program product, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of the preferred embodiments of the invention has been presented for purposes of illustration and description. They are not intended to be exhaustive or to limit the invention to the precise form disclosed, and obviously many modifications and variations are possible in light of the above teachings. Such modifications and variations that are apparent to a person skilled in the art are intended to be included within the scope of this invention as defined by the accompanying claims.

The invention claimed is:

1. A customer relationship management (CRM) system that is accessible via a network, comprising:
   a computer system, comprising at least one computing device, the computer system including:
   a user interface that provides distributed access for customers and support providers to case information within the CRM system, wherein the customers and the support providers are separate and distinct institutions; and wherein the user interface provides access to both customers and support providers to a customer case management page for viewing all cases opened for a given customer and a case summary page for viewing details of individual cases stored within the CRM system;
   wherein a customer case includes a request from the customer to the support provider for support;
   a case management system for managing customer cases, wherein the case management system includes a system for assigning cases to different tiers within a support provider hierarchy, determining whether an assigned tier can resolve the case, and escalating the case to a different tier in response to a determination that the assigned tier cannot resolve the case; and
   a compliance tracking system that retrieves previously loaded customer compliance data from a database; wherein the compliance data consists of information related to whether a customer has met certain required pre-set goals set by the CRM system, compares the compliance data for each customer with predetermined levels to determine customer compliance, provides a compliance indicator on the customer case management page that indicates whether a compliance issue exists, and escalates the case to a different tier in response to an existence of a compliance issue.

2. The CRM system of claim 1, wherein the case management system further includes a notification system for automatically generating emails when a new case is opened.

3. The CRM system of claim 1, wherein the case management system further includes a system that allows support providers to check-in/check-out cases.

4. The CRM system of claim 1, wherein the case management system further includes a set of business rules that determines what level of case information is to be made available to customers and support providers.

5. The CRM system of claim 1, wherein the case management system further includes a set of business rules that determines how cases are to be assigned and escalated among the different tiers of support providers.

6. The CRM system of claim 1, wherein the compliance tracking system includes a set of business rules that determines a compliance risk level for each customer.

7. The CRM system of claim 6, wherein the compliance risk level is selected from the group consisting of: in compliance, in danger of becoming out of compliance, and out of compliance.

8. The CRM system of claim 7, wherein the compliance indicator comprises a traffic light indicator having a green, yellow and red light.

9. The CRM system of claim 6, wherein the compliance tracking system includes a system for creating a new customer case when a predetermined compliance risk level occurs.

10. A method for providing customer relationship management (CRM) via a computer network, comprising:
    providing a network node that allows distributed access for customers and support providers to a CRM system using a computer system, comprising at least one computing device, wherein the customers and the support providers are separate and distinct institutions;
    opening a new case within the CRM system when a customer issue occurs using the computer system;
    wherein the customer issue includes a request from the customer to the support provider for support;
    adding the new case to a customer case management page using the computer system; wherein both
    customers and support providers have access to the customer case management page;
    displaying a compliance indicator when the customer case management page is viewed using the computer system; wherein the compliance indicator indicates whether a compliance issue exists and is based on information related to whether a customer has met certain required pre-set goals set by the CRM system,
    assigning the new case to a first tier support provider using the computer system;
    determining whether the first tier support provider can handle the new case using the computer system; and
    escalating the new case to a second tier support provider in the case that the first tier support provider cannot handle the case or if a compliance issue exists using the computer system.

11. The method of claim 10, wherein the network node comprises a web portal.

12. The method of claim 10, wherein the compliance indicator determines if the customer is in compliance, at risk of becoming out of compliance, or out of compliance.

13. The method of claim 10, comprising the further step of generating email notifications according to a set of business rules using the computer system.

14. The method of claim 10, comprising the further step of having an assigned support provider check out the case from the CRM system using the computer system.

15. The method of claim 10, wherein the step of opening a new case is performed by the customer at the network node.

16. The method of claim 10, wherein the step of opening a new case is initiated automatically when the customer is out of compliance.

17. The method of claim 10, wherein the compliance indicator comprises a traffic light indicator having a green, yellow and red light.

18. A program product stored on a recordable storage medium that provides a customer relationship management (CRM) tool via the web, comprising:
    a portal page for providing distributed access on the web for customers and support providers to case information within the CRM tool, wherein the customers and the support providers are separate and distinct institutions; and wherein the portal page provides access to a customer case management page for viewing all cases opened for a given customer and a case summary page for viewing details of individual cases, wherein both customers and support providers have access to the customer case management page and the case summary page; wherein a customer case includes a request from the customer to the support provider for support;
    a customer management module for managing customer cases and for assigning cases to different tiers within a support provider hierarchy; and a customer compliance module that retrieves previously loaded customer compliance data from a database; wherein the compliance data consists of information related to whether a customer has met certain required pre-set goals set by the CRM system, compares the compliance data for each customer with predetermined levels to track customer compliance and displays a compliance indicator on the customer case management page that indicates whether a compliance issue exists, and escalates the case to a different tier in response to an existence of a compliance issue.

19. The program product of claim 18, wherein the case management module further includes a notification system for automatically generating emails when a new case is opened.

20. The program product of claim 18, wherein the case management module further includes a system that allows support providers to check-in/check-out cases.

21. The program product of claim 18, wherein the case management module further includes a set of business rules that determines what level of case information is to be made available to customers and support providers.

22. The program product of claim 18, wherein the case management module further includes a set of business rules that determines how cases are to be assigned and escalated among the different tiers of support providers.

23. The program product of claim 18, wherein the compliance tracking module includes a set of business rules that determines a compliance risk level for each customer.

24. The program product of claim 23, wherein the compliance risk level is selected from the group consisting of: in compliance, in danger of becoming out of compliance, and out of compliance.

25. The program product of claim 23, wherein the compliance indicator comprises a traffic light indicator having a green, yellow and red light.

26. The program product of claim 23, wherein the compliance tracking module includes a system for creating a new customer case when a predetermined compliance risk level occurs.

* * * * *